United States Patent [19]

Iglesia et al.

[11] Patent Number: 4,794,099

[45] Date of Patent: Dec. 27, 1988

[54] SIO₂-PROMOTED COBALT CATALYST ON A SUPPORT OF TIO₂ FOR CONVERTING SYNTHESIS GAS TO HEAVY HYDROCARBONS

[75] Inventors: Enrique Iglesia, Clinton; Stuart Soled, Pittstown; Rocco A. Fiato, Basking Ridge, all of N.J.

[73] Assignee: Exxon Research and Engineering Company, Florham Park, N.J.

[21] Appl. No.: 7,494

[22] Filed: Jan. 28, 1987

[51] Int. Cl.⁴ .................... B01J 21/06; B01J 21/08; B01J 23/84

[52] U.S. Cl. .................................. 502/241; 502/242

[58] Field of Search ............... 502/241, 242, 325; 518/715

[56] References Cited

U.S. PATENT DOCUMENTS

| | | | |
|---|---|---|---|
| 3,159,569 | 12/1964 | Hansford | 502/242 X |
| 4,499,209 | 2/1985 | Hoek et al. | 502/242 X |
| 4,568,663 | 2/1986 | Mauldin | 502/325 |
| 4,681,867 | 7/1987 | Dyer et al. | 502/242 |

Primary Examiner—W. J. Shine
Attorney, Agent, or Firm—Jay Simon

[57] ABSTRACT

An improved hydrocarbon synthesis catalyst is prepared incorporating limited amounts of silica or a silica precursor to a catalyst comprising cobalt or an inorganic refractory support comprised primarily of titania.

8 Claims, 2 Drawing Sheets

SIO₂-PROMOTED COBALT CATALYST ON A SUPPORT OF TIO₂ FOR CONVERTING SYNTHESIS GAS TO HEAVY HYDROCARBONS

FIELD OF THE INVENTION

This invention relates to a catalyst of improved activity for the production of hydrocarbons from synthesis gas, hydrogen and carbon monoxide, and to an improved hydrocarbon synthesis process. Specifically, this invention relates to a catalyst comprising cobalt on at least a predominantly titania support to which small amounts of silica are added. The resulting catalyst is more active with regard to carbon monoxide conversion than catalysts not containing the added silica and allows reduced operating temperatures for hydrocarbon synthesis and thereby a reduction in methane selectivity and concomitant increases in $C_{5+}$ yield.

PRIOR ART

Methane is available in large quantities in many areas of the world. Some methane is generated from refinery applications while large amounts of methane, as the principal constituent of natural gas, are found in deposits in various areas. Methane can be used as a gas, for example, for heating purposes, and can be transported by pipeline or as a liquefied gas over long distances. Where use of the methane as a gas is not economic or the transportation of methane requires traversing oceans, the methane can be converted to a liquid which is more easily transported and may have significantly higher value than methane gas.

Conversion of methane is normally carried out in a two-step procedure involving reforming the methane to produce hydrogen and carbon monoxide, synthesis gas and converting the synthesis gas to higher hydrocarbons, $C_{5+}$, in a Fischer-Tropsch type reaction. Both steps of the process are well known and can be readily illustrated: the first step by U.S. Pat. Nos. 1,711,036 1,960,912 and 3,138,438; and second step by U.S. Pat. Nos. 4,477,595 4,542,122, and 4,088,671.

This invention is concerned with the second step, the well known Fischer-Tropsch reaction which is referred to hereinafter as hydrocarbon synthesis.

This invention is primarily concerned with cobalt containing catalysts for hydrocarbon synthesis which have been disclosed as being useful in such reactions, either alone or jointly with other materials. What has not been disclosed in the art is the combination of steps required to produce a composition that is novel and has superior catalytic activity properties relative to other cobalt containing catalysts. These properties include: improved CO conversion, improved volumetric productivity, enhanced selectivity to $C_{5+}$ and lower $CH_4$ production. U.S. Pat. No. 4,542,122 discloses a cobalt or cobalt-thoria on titania catalyst for hydrocarbon synthesis having a preferred ratio of rutile to anatase. U.S. Pat. No. 4,568,663 discloses a high activity hydrocarbon synthesis catalyst comprising cobalt and rhenium on a titania support. U.S. Pat. No. 4,413,064 discloses an alumina supported catalyst having cobalt, ruthenium and a Group IIIA or Group IVB metal oxide, e.g., thoria. European patent application No. 86/180269A discloses a silica supported cobalt catalyst to which a silicon compound has been added prior to addition of the catalytic metal.

SUMMARY OF THE INVENTION

A substantial increase in the activity of cobalt catalysts supported on titania can be achieved when silica is added to the catalyst. For purposes of this invention activity may be measured as cobalt-time yield (defined as the moles of carbon monoxide converted per hour per gram-atom of cobalt in the catalyst) or as cobalt site-time yield (defined as the moles of carbon monoxide converted per hour per surface cobalt atom in the catalyst). In either case, activity increases in excess of 40%, preferably in excess of 50%, may be obtained by practicing this invention.

Figure 1:
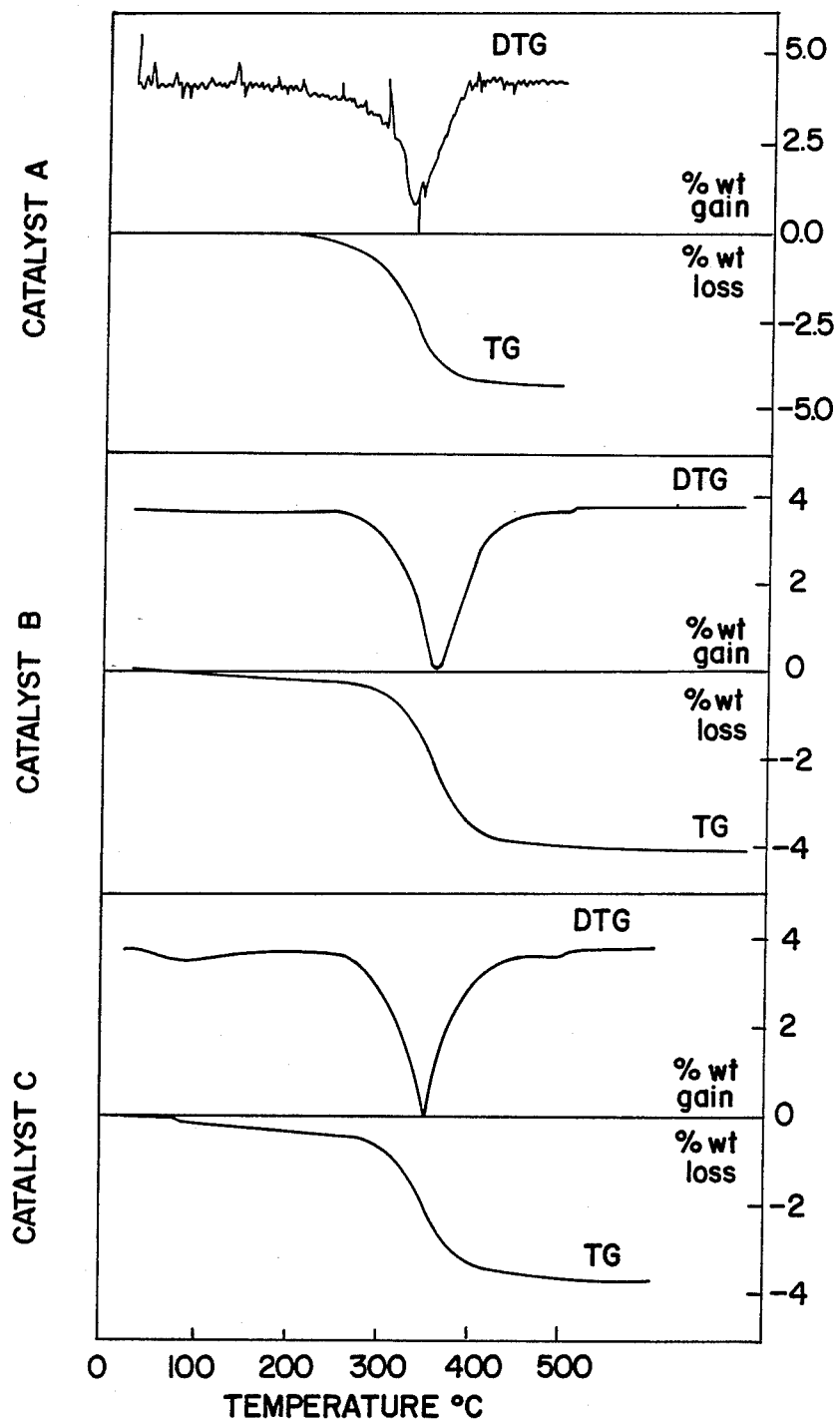
FIG. 1 shows the weight change and rate of weight change for catalysts A, B, and C at atmospheric pressure. The TC curve monitors weight changes as the supported cobalt oxide is reduced in hydrogen from room temperature to 500° C. at 6 deg/min. The DTG curve plots the rate of weight change with time as a function of temperature.

Neither silicon nor silica are known to promote hydrogenolysis of coke or carbon deposits and the increase in activity cannot be accounted for on the basis of hydrogenation of carbon deposits on the catalyst. Because the increase in activity occurs immediately in the course of hydrocarbon synthesis, the silica may be reacting with or in some way tying up specific sites on the surface of the support, titania, that would otherwise promote the formation of carbon. The presence of silica may act, therefore, to retard carbon formation on the catalyst. Indirect evidence suggests that the silica is in close proximity to the cobalt and may even block some cobalt sites because the degree of cobalt dispersion, after addition of the silica, is somewhat less than the cobalt dispersion without added silica. Regardless of the theoretical explanation for the increased activity of the catalyst, this invention is based on the presence of sufficient silica to increase catalyst activity vis-a-vis a catalyst that has no added silica.

European patent application No. 86/180269A discloses the addition of a silicon containing compound to cobalt containing catalysts supported on silica and an increase in catalyst activity is claimed. They claim that the silicon containing compound prevents the subsequently applied cobalt from reacting with silicates present as a result of the use of a silica support and, therefore, more cobalt is available for use as a catalytic metal in hydrocarbon synthesis. The addition of the silicon containing compound prevents the formation of hydroxy silicates that effectively tie up some of the cobalt. This invention utilizes a titania containing support and does not utilize a silica containing support and the explanation of the increased activity in the application does not apply in this invention. Cobalt does not tie up titanates the way it ties up with silicates in a silica containing support and the chemisorption measurements show that the amount of cobalt available actually decreases when silica is added to the catalyst of this invention.

DETAILED DESCRIPTION

By virtue of what we believe to be happening in this invention, any amount of added silica to the catalyst will improve catalyst activity. On the other hand, too much silica should not be added because the available cobalt is reduced sufficiently to overcome the advantage of adding silica, for example, available cobalt may be reduced by masking by the silica. Also, the cobalt may tie up with silicates if too much silica is added.

Generally, silica additions may range up to about 15% by weight, preferably about 1 wt.% to about 10 wt.% catalyst, and more preferably 3 to 7 wt.%.

Silica can be added to the catalyst with any suitable compound that will result in $SiO_2$ upon decomposition, for example, as an alkoxide solution (tetraethyl orthosilicate in methanol). Other precursors for silica that are usable in this invention are described in European patent application No. 86/180269A.

The silica or silica precursor may be added to the support either before or after addition of catalytic metals. Either method will produce the results disclosed herein although addition of silica or silica precursor after addition of catalytic metals is preferred.

Catalysts that may be employed in this invention comprise cobalt or cobalt and thoria on an inorganic oxide support containing a major amount of titania. The catalyst may also contain a promoter metal, preferably rhenium, in an amount sufficient to provide a catalyst having a rhenium:cobalt weight ratio greater than about 0.01 to 1, preferably 0.025:1 to about 0.1 to 1. The catalyst contains about 2 to 25 wt.% cobalt, preferably 5 to 20 wt.% cobalt.

In general, the hydrocarbon synthesis reaction is carried out at conditions that are known in the art. The $H_2$:CO ratio is at least about 0.5 up to about 10, preferably 0.5 to 4.0, and more preferably about 1.0 to 2.5. The gas hourly space velocity can range from about 100 v/hr/v to about 5000 v/hr/v, preferably from about 300 v/hr/v to about 1500 v/hr/v and reaction temperatures may range from about 160° C. to about 300° C., preferably about 190° C. to 260° C., while pressures are above about 80 psig, preferably about 80 to 600 psig, more preferably about 140 to 400 psig. Hydrocarbon synthesis results in the formation of hydrocarbons of carbon number range $C_5$ to about $C_{40}$ or higher. Preferably, the synthesized hydrocarbons are primarily or almost completely paraffins. Reaction temperatures, while generally in the range accepted for this type of reaction may be in the lower regions of that range, thereby reducing the amount of methane made during the reaction.

The catalytic metals are supported on an inorganic refractory oxide support comprising a major portion of titania although other materials, e.g., alumina, may be present. Preferably, the support material is titania and more preferably the titania has a rutile:anatase ratio of at least about 2:3 as determined by x-ray diffraction (ASTM D2730-78), preferably about 2:3 to about 100:1 or higher, more preferably about 4:1 to 100:1 or higher, e.g., 100% rutile. The surface area of the support is, generally, less than about 50 m²/gm (BET).

Rhenium-cobalt/titania catalysts exhibit high selectively in the synthesis of hydrocarbon liquids from carbon monoxide and hydrogen. The catalysts employed in the practice of this invention may be prepared by techniques known in the art for the preparation of other catalysts. The catalyst can, e.g., be prepared by gellation, or cogellation techniques. Suitably, however, the metals can be deposited on a previously pilled, pelleted, beaded, extruded, or sieved support material by the impregnation method. In preparing catalysts, the metals are deposited from solution on the support in preselected amounts to provide the desired absolute amounts, and weight ratio of the respective metals, cobalt and rhenium. Suitably, the cobalt and rhenium are composited with the support by contacting the support with a solution of a cobalt-containing compound, or salt, or a rhenium-containing compound, or salt, e.g., a nitrate, carbonate or the like. Optionally, the cobalt and rhenium can be co-impregnated upon the support. The cobalt and rhenium compounds used in the impregnation can be any organometallic or inorganic compounds which decompose to give cobalt, rhenium oxides upon calcination, such as a cobalt or rhenium, nitrate, acetate, acetylacetonate, naphthenate, carbonyl, or the like. The amount of impregnation solution should be sufficient to completely wet the carrier, usually within the range from about 1 to 20 times of the carrier by volume, depending on the metal, or metals, concentration in the impregnation solution. The impregnation treatment can be carried out under a wide range of conditions including ambient or elevated temperatures.

The catalyst, after impregnation, is dried by heating at a temperature above about 30° C., preferably between 30° C. and 125° C., in the presence of nitrogen or oxygen, or both, or air, in a gas stream or under vacuum. It is necessary to activate the cobalt-titania and promoted cobalt-titania catalysts prior to use. Preferably, the catalyst is contacted with oxygen, air, or other oxygen-containing gas at temperature sufficient to oxidize the cobalt, and convert the cobalt to $Co_3O_4$. Temperatures ranging above about 150° C., and preferably above about 200° C. are satisfactory to convert the cobalt to the oxide, but temperatures up to about 500° C. such as might be used in the regeneration of a severely deactivated catalyst, can generally be tolerated. Suitably, the oxidation of the cobalt is achieved at temperatures ranging from about 150° C. to about 300° C. The cobalt, or cobalt and rhenium metals contained in the catalyst are then reduced. Reduction is performed by contact of the catalyst, whether or not previously oxidized, with a reducing gas, suitably with hydrogen or a hydrogen-containing gas stream at temperatures above about 200° C., preferably above about 300° C. Suitably, the catalyst is reduced at temperatures ranging from about 200° C. to about 500° C., and preferably from about 300° C. to about 450° C., for periods ranging from about 0.5 to about 24 hours at pressures ranging from ambient to about 40 atmospheres. Hydrogen, or a gas containing hydrogen and inert components in admixture is satisfactory for use in carrying out the reduction.

EXAMPLES

Catalyst Preparation

CoRe/TiO2 [Catalyst A]

Degusa P25 $TiO_2$ was calcined at 650° C. for 16 hours and then screened to 80–150 mesh size. The support had a rutile content of 97%, a surface area of 14 m2/g and a pore volume of 0.17 cm³/g.

Cobalt and rhenium were deposited on to this support from an acetone solution using a slurry technique. The slurry was dried at room temperature in a rotary evaporator and then in vacuum at 140° C. for 16 hours. It was then calcined at 250° C. for 3 hours and rescreened to remove fines. The catalyst was then reduced before chemisorption and hydrocarbon synthesis measurements at conditions described below (flowing hydrogen 250°–450° C.). The Co and Re contents of the reduced catalyst were 11.6 and 0.43–0.48 wt.%, respectively (x-ray fluorsecence).

$SiO_2$-Promoted CoRe/$TiO_2$ (Catalysts B and C)

$SiO_2$ was deposited onto an unreduced CoRe/$TiO_2$ [catalyst A] by incipient wetness impregnation with a solution of tetraethoxysilane (TEOS) in methanol in an inert atmosphere ($N_2$). TEOS was decomposed by treating with water-saturated He (40 Torr $H_2O$) while increasing the temperature from 25° to 400° C. at 4° C./min and holding at the latter temperature for 13 hours. The catalysts were reduced at 250°–450° C. for 2–14 hours before chemisorption and hydrocarbon synthesis experiments. Two $SiO_2$ contents were examined: 4.0 wt.% [Catalyst B] and 5.2 wt.% [Catalyst C], on the basis of completely reduced catalysts; their cobalt content was 10.8–11.1 wt.%. $SiO_2$ loadings were lower than calculated from the amount of impregnating solution (5.0 and 9.0 wt.%., respectively), suggesting some sublimation of the supported TEOS material during the steam treatment.

Water-Treated CoRe/$TiO_2$ [Catalyst D]

A portion of Catalyst A was pretreated in water-saturated He (40 Torr $H_2O$) following the procedure used for Catalysts B and C, but without $SiO_2$ addition in order to insure that any observed effects of added $SiO_2$ are not caused by the pretreatment procedure. The catalyst was then reduced as described above.

Catalyst Characterization

Chemisorption

Molecular hydrogen was used as a probe of surface cobalt atoms in hydrocarbon synthesis catalysts.

Dihydrogen uptakes were measured in an all-glass static chemisorption unit, pumped by diffusion and roughing pumps isolated from the system by liquid nitrogen traps, and capable of a dynamic vacuum of $10^{-7}$ Torr. Prereduced and passivated samples were rereduced in flowing dihydrogen (200 $cm^3$(STP)/g-cat-min) for 1–2 hours at 200°–800° C., and then evacuated to less than $10^{-6}$ Torr for 0.5–1 hr. at a temperature sufficient to remove all chemisorbed hydrogen (>250° C.). The samples were then cooled to the adsorption temperature (25° to 150° C.) and isotherms were measured at 3 to 5 hydrogen pressures between 100 and 700 Torr. A backsorption isotherm was sometimes measured by evacuating the sample to $10^{-6}$ Torr at the adsorption temperature for 0.5 hour and then measuring the hydrogen uptakes again between 100 and 600 Torr. Adsorption and backsorption isotherms were extrapolated to zero pressure to obtain the total and weak chemisorption uptakes, respectively.

Dispersions were calculated from hydrogen uptakes and from the cobalt content of the samples, assuming 1:1 stoichiometry of hydrogen to surface cobalt atoms. Dispersions were converted to surface-averaged crystallite sizes (d), assuming hemispherical crystallites, using:

$$d/\text{Å} = 9.5/D$$

where D is the fractional dispersion, assuming cobalt crystallites form in fcc structures with a random distribution of (111), (110), and (100) crystallographic planes.

Thermogravimetric Analysis Procedure

A Mettler TA 2000C thermal balance measured both weight changes (TG) and rates of weight change (DTG) in $H_2$, CO, or 1:1 $H_2$/CO mixtures, at atmospheric pressure. Peaks in the derivative weight curve correspond to maximum rates of weight change. Gas flows were set at 100 $cm^3$ (STP)/min and 150 mg catalyst samples were used. A 6° C./min temperature program was adopted as a standard heating rate. All samples were reduced in $H_2$ from room temperature to 500° C. Following the $H_2$ treatment, the sample was cooled and treated in 1:1 $H_2$/CO mixture. The growth of an amorphous carbon phase was used to determine intimate contact and strong interactions between cobalt and silica. Powder x-ray diffraction spectra, taken before and after the runs confirmed the phases present.

Hydrocarbon Synthesis Procedure

Steady-state kinetics and residence time studies were measured in a plug-flow fixed-bed reactor at 180°–230° C., 100–2050 kPa, and $H_2$/CO of 2/1 using 2–10 g of catalyst. Catalysts were reduced in hydrogen at 250°–450° C., cooled to synthesis temperature, and exposed to $H_2$/CO feed. All reported data were obtained after at least 24 hours on stream. Standard conditions are 200° C., 2050 kPa, and $H_2$/CO of 2/1. Products were analyzed by capillary and packed column gas chromatography and GC/MS, using dinitrogen as an internal standard. $C_{20}+$ distributions were obtained by gas chromatography and gel permeation chromatography.

Hydrocarbon synthesis rates are reported as cobalt-normalized rates (cobalt-time yields), defined as the moles of CO converted per hour per g-atom cobalt in the catalysts, as site-normalized rates (site-time yields), defined as the molecules of CO converted per hour per surface cobalt atom in the catalysts, and as volumetric rates, defined as the volume of CO converted per volume of catalyst per hour. Hydrocarbon selectivities are reported on a carbon atom basis, as the percentage of the converted CO that appears as a given product. Reported chain growth probabilities are asymptotic values, obtained from the constant slope of Flory plots for $C_{35}$–$C_{100}$ hydrocarbons.

Example 1: Effect of $SiO_2$ Addition on Hydrocarbon Synthesis Performance of CoRe/$TiO_2$ The addition of small amounts of $SiO_2$ (4–6 wt.%) to CoRe/$TiO_2$ increases the cobalt time yield in spite of the decrease in cobalt dispersion that occurs during the pretreatment required in order to decompose the $SiO_2$ precursor (Table 1 and 2). The apparent intrinsic activity of a cobalt surface atom (site-time yield) actually increases two-fold with the addition of 4–6 wt.% $SiO_2$. Hydrocarbon synthesis selectivity is almost unchanged by $SiO_2$ addition; $CH_4$ selectivity is 5.0–5.4 wt.% and $C_5+$ selectivity is 88.8–90% on these catalysts. The olefin content increases with $SiO_2$ addition for $C_5+$ hydrocarbons. Treatment of CoRe/$TiO_2$ with He/$H_2O$ at 400° C., decreased cobalt dispersion to the level measured on $SiO_2$ containing samples subjected to the same pretreatment. The cobalt time yield is lower than on fresh CoRe/TiO$_2$ because of the lower dispersion, but the site-time yields are identical.

Activity maintenance is at least equal to that of CoRe/TiO$_2$ catalysts not containing silica. However, because of their high initial activity, SiO$_2$-promoted catalysts maintain a higher level of productivity throughout a cycle.

lyst preparation, pretreatment, and use in hydrocarbon synthesis. The effect of SiO$_2$ during carburization suggests that SiO$_2$ may prevent the short term deactivation observed on these catalysts during the first few hours in H$_2$/CO environments; the effect is to increase the apparent site activity by maintaining surface cobalt atoms available during hydrocarbon synthesis.

TABLE 1

EFFECT OF SiO$_2$ PROMOTION (47-50 H ON STREAM)

| Catalyst | A | D | B | C |
|---|---|---|---|---|
| Percent SiO$_2$ | 0 | 0 | 4 | 5.2 |
| Pretreatment: He/H$_2$O, 400° C. | No | Yes | Yes | Yes |
| H$_2$/450° C. | Yes | Yes | Yes | Yes |
| Run | 110-19 | 41-174 | 37-62 | 39-124 |
| Time on Stream (hr) | 50.0 | 49.1 | 47 | 49 |
| CO Conversion (%) | 61.5 | 67 | 69 | 60 |
| Cobalt-time yield (moles CO converted/g-atom Co-hr) | 5.7 | 5.1 | 7.5 | 8.3 |
| Site-time yield (moles CO converted/g-atom surface Co-hr) | 90 | 98 | 145 | 150 |
| Volumetric Productivity (cc CO converted/cc CAT. hr) | 310 | 275 | 410 | 450 |
| Cobalt Dispersion (%) | 6.5 | 5.3 | 5.2 | 5.6 |
| Carbon Selectivity (%) | | | | |
| CH$_4$ | 5.3 | 4.6 | 5.2 | 5.4 |
| C$_2$ [O/P] | 0.6[.12] | 0.6[.17] | 0.7[.11] | 0.6[.13] |
| C$_3$ [O/P] | 2.1[1.9] | 2.2[2.6] | 2.4[2.0] | 2.3[2.0] |
| C$_4$ [O/P] | 2.3[.70] | 2.0[1.6] | 2.4[1.1] | 2.6[1.2] |
| C$_5$+ | 89.5 | 90.3 | 89.3 | 89.1 |
| CO$_2$ | 0.2 | 0.3 | 0.07 | 0.05 |

Conditions: 200° C., 2100 kPa, H$_2$/CO = 2/1, 60% CO conversion
(1) From hydrogen chemisorption measurements at 100° C., assuming a 1:1 H:surface Co stiochiometry

TABLE 2

EFFECT OF SiO$_2$ PROMOTION (120-190 H on Stream)

| Catalyst | A | D | B | C |
|---|---|---|---|---|
| Percent SiO$_2$ | 0 | 0 | 4 | 5.2 |
| Pretreatment: He/H$_2$O, 400° C. | No | Yes | Yes | Yes |
| H$_2$/450° C. | Yes | Yes | Yes | Yes |
| Run | 110-28 | 41-188 | 37-71 | 39-133 |
| Time on Stream (hr) | 139 | 190 | 120 | 119 |
| CO Conversion (%) | 64 | 58 | 61 | 55 |
| Cobalt-time yield (moles CO converted/g-atom Co-hr) | 5.5 | 4.4 | 6.8 | 7.5 |
| Site-time yield (moles CO converted/g-atom surface Co-hr) | 85 | 85 | 131 | 135 |
| Volumetric Productivity (cc CO converted/cc CAT. hr) | 295 | 240 | 370 | 410 |
| Cobalt Dispersion (%) | 6.5 | 5.3 | 5.2 | 5.6 |
| Carbon Selectivity | | | | |
| CH$_4$ | 5.1 | 5.0 | 5.6 | 5.8 |
| C$_2$ [O/P] | 0.6[.14] | 0.6[.19] | 0.7[.13] | 0.6[.14] |
| C$_3$ [O/P] | 1.9[2.1] | 2.1[2.8] | 2.5[2.1] | 2.3[2.1] |
| C$_4$ [O/P] | 2.16[.63] | 1.9[1.6] | 2.6[1.3] | 2.5[1.3] |
| C$_5$+ | 89.9 | 90.1 | 88.5 | 89.1 |
| CO$_2$ | 0.2 | 0.3 | 0.06 | 0.04 |

Conditions: 200° C., 2100 kPa, H$_2$/CO = 2/1, 60% CO conversion
(1) from hydrogen chemisorption measurements at 100° C., assuming a 1:1 H:surface Co stoichiometry Example 2: Effect of SiO$_2$ Addition on Reduction and Carburization Properties of CoRe/TiO$_2$ The addition of SiO$_2$ to CoRe/TiO$_2$ did not affect its reduction behavior. The temperature-programmed reduction profiles and the extent of reduction at 450° C. were identical in SiO$_2$-promoted and unpromoted samples (FIG. 1)

Figure 2:
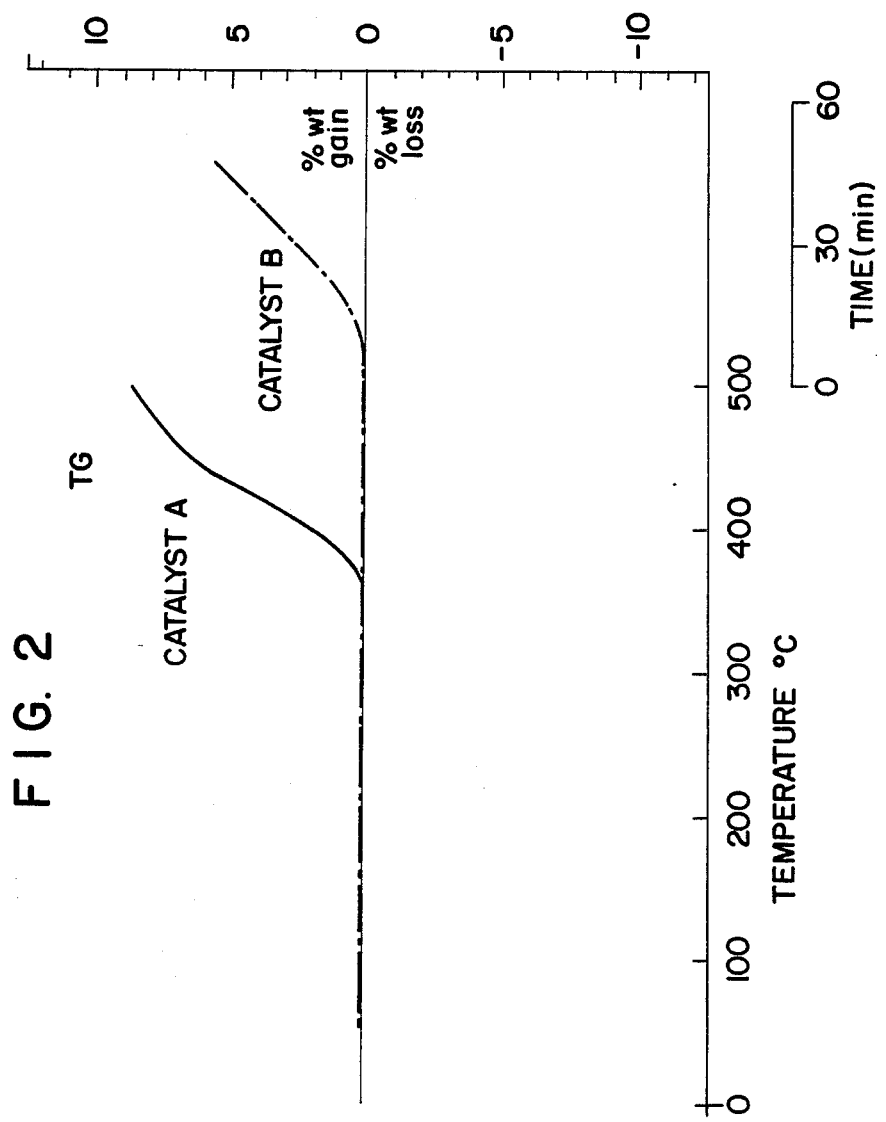
FIG. 2 shows the effect on catalysts A and B of carburization, i.e., the tendency of carbon to grow on active sites, in a synthesis gas environment. Catalyst B shows a weight gain due to carbon growth at a much higher temperature than for catalyst A showing that the presence of silica suppresses carbon growth.

Carburization of the catalysts was dramatically inhibited by SiO$_2$ addition (FIG. 2). The addition of 4 wt.% SiO$_2$ delays the onset of carburization from 370° C. to 500° C. during temperature-programmed treatment with H$_2$/CO mixtures (1/1 ratio). Similar results were obtained at higher SiO$_2$ loadings.

These data suggest that the role of SiO$_2$ is not to improve the reducibility of cobalt oxide precursors or to prevent the formation of cobalt titanates during cata- SiO$_2$ is known to adsorb onto strong acid sites in Al$_2$O$_3$, to modify hydroxyl groups and acid sites in fused silica tubing, and to prevent carburization of stainless steel reactor walls. We believe that SiO$_2$ titrates or modifies specific sites on Co/TiO$_2$ catalysts, decreasing their activity for carbon formation. Decoration of the cobalt surface with SiO$_2$, and inhibition of carbon deposition by the accompanying decrease in available cobalt ensemble size in unlikely. If so, the addition of SiO$_2$ would have decreased the hydrogen uptake, and the apparent dispersion, more than the He/H$_2$O treatment did (Table 1).

A decrease in catalyst acidity with SiO$_2$ addition is consistent with the observed decrease in the internal olefin and branched product selectivity of the C$_6$+ hydrocarbons when SiO$_2$ was introduced in the TiO$_2$- supported cobalt catalyst (Table 3). Internal olefins are branched products and are usually associated with double bond and skeletal isomerization of primary alpha-olefin products on metal and oxide catalysts.

TABLE 3

EFFECT OF SiO$_2$ ADDITION ON THE SELECTIVITY TO INTERNAL OLEFINS AND BRANCHED PRODUCTS

| C$_6$ hydrocarbons | Run | | |
|---|---|---|---|
| | 110-28 | 37-65 | 39-124 |
| | Catalyst | | |
| | A | B | C |
| % 3-hexene in C$_6$ | 1.7 | 1.7 | 2.3 |
| % 2-hexene in C$_6$ | 12.8 | 11.4 | 8.9 |
| % methyl-hexanes in C$_6$ | 2.6 | 1.6 | 1.9 |

What is claimed is:

1. A hydrocarbon synthesis catalyst comprising cobalt in a catalytically active amount composited with an inorganic refractory support comprised of a major portion of titania to which a lesser portion up to about 15 wt.% of silica in the form of silica or a silica precursor has been added.

2. The catalyst of claim 1 wherein the silica is present in an amount sufficient to increase the site time yield in a hydrocarbon synthesis process over the site time yield obtained for that catalyst without silica.

3. The catalyst of claim 2 wherein rhenium is present in catalytically active amounts.

4. In a process for preparing a hydrocarbon synthesis catalyst comprising catalytically active amounts of cobalt on a support comprised primarily of titania, the improvement which comprises adding to the support up to about 15 wt.% silica in the form of silica or a silica precursor.

5. The catalyst of claim 1 wherein the titania has a rutile:anatase ratio of at least 2:3.

6. The catalyst of claim 1 wherein the titania is 100% rutile.

7. The process of claim 4 wherein the silica or silica precursor is added to the support prior to incorporation of the cobalt.

8. The process of claim 4 wherein the silica or silica precursor is added to the support subsequent to incorporation of the cobalt.

* * * * *